(12) United States Patent
Erickson et al.

(10) Patent No.: US 6,754,539 B1
(45) Date of Patent: *Jun. 22, 2004

(54) SPINAL CORD STIMULATION LEAD WITH AN ANODE GUARD

(75) Inventors: John H. Erickson, Plano, TX (US); Scott F. Drees, McKinney, TX (US)

(73) Assignee: Advanced Neuromodulation Systems, Inc., Plano, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/635,910

(22) Filed: Aug. 10, 2000

(51) Int. Cl.[7] ............................................. A61N 1/18
(52) U.S. Cl. ...................................................... 607/117
(58) Field of Search ............................... 600/373, 393; 607/117

(56) References Cited

U.S. PATENT DOCUMENTS

| | | | |
|---|---|---|---|
| 4,379,462 A | | 4/1983 | Borkan et al. .............. 128/786 |
| 4,448,199 A | * | 5/1984 | Schmid ....................... 128/639 |
| 5,119,832 A | | 6/1992 | Xavier ........................ 128/786 |
| 5,417,719 A | * | 5/1995 | Hull et al. .................... 607/46 |
| 5,643,330 A | | 7/1997 | Holsheimer et al. .......... 607/46 |
| 5,895,416 A | * | 4/1999 | Barreras, Sr. et al. ........ 607/62 |
| 5,935,082 A | * | 8/1999 | Albrecht et al. ............ 600/515 |
| 6,038,480 A | * | 3/2000 | Hrdlicka et al. ............ 607/116 |
| 6,205,361 B1 | * | 3/2001 | Kuzma et al. .............. 607/116 |
| 6,236,892 B1 | * | 5/2001 | Feler .......................... 607/117 |
| 6,505,078 B1 | * | 1/2003 | King et al. ................... 607/67 |

* cited by examiner

*Primary Examiner*—Jeffrey R. Jastrzab
*Assistant Examiner*—Frances P. Oropeza
(74) *Attorney, Agent, or Firm*—Koestner Bertani LLP

(57) ABSTRACT

The present invention relates to an epidural stimulation lead having at least one electrode that substantially encircles another electrode. Operatively, the encircling electrode can be set as an, anode and the encircled electrode can be set as a cathode to generate an electrical field therebetween. The encircling electrode functions in this capacity as an anode guard, which among other things, concentrates the electrical field about the designated cathode and limits the lateral range of a generated electrical field.

26 Claims, 2 Drawing Sheets

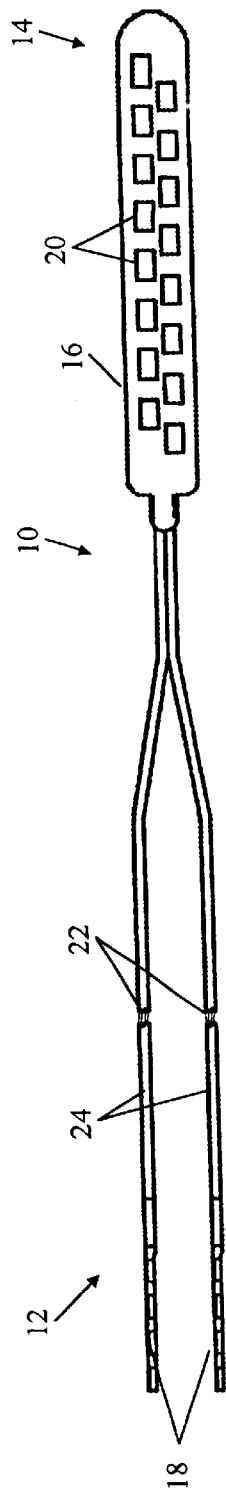
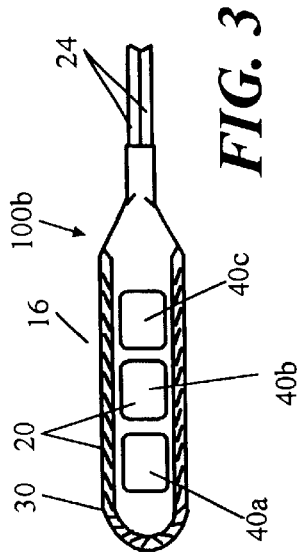
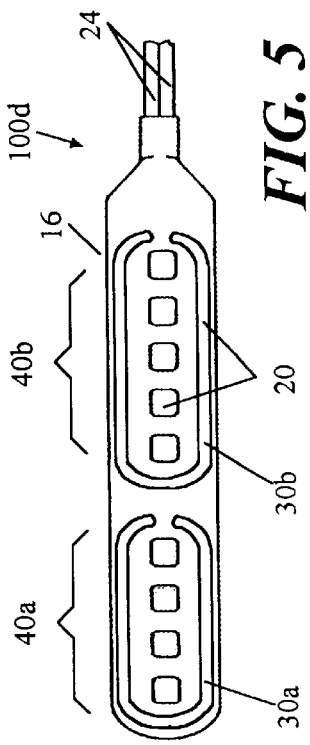
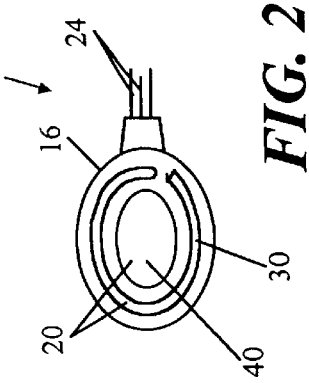
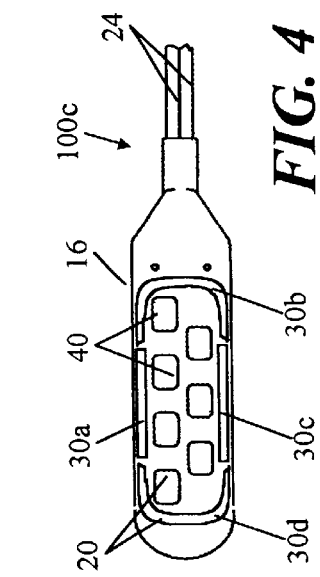
FIG. 1 Prior Art
FIG. 2
FIG. 3
FIG. 4
FIG. 5

SPINAL CORD STIMULATION LEAD WITH AN ANODE GUARD

OF THE INVENTION

The present invention relates to an epidural stimulation lead, and in particular, to an epidural stimulation lead having at least one electrode suited to serve as an anode guard relative to a substantially encircled cathode.

BACKGROUND OF THE INVENTION

Application of specific electrical fields to spinal nerve roots, spinal cord, and other nerve bundles for the purpose of chronic pain control has been actively practiced since the 1960s. While a precise understanding of the interaction between the applied electrical energy and the nervous tissue is not fully appreciated, it is known that application of an electrical field to spinal nervous tissue (i.e., spinal nerve roots and spinal cord bundles) can effectively mask certain types of pain transmitted from regions of the body associated with the stimulated tissue. More specifically, applying particularized electrical energy to the spinal cord associated with regions of the body afflicted with chronic pain can induce paresthesia, or a subjective sensation of numbness or tingling, in the afflicted bodily regions. This paresthesia can effectively mask the transmission of non-acute pain sensations to the brain.

It is known that each exterior region, or each dermatome, of the human body is associated with a particular spinal nerve root at a particular longitudinal spinal position. The head and neck regions are associated with C2–C8, the back regions extends from C2–S3, the central diaphragm is associated with spinal nerve roots between C3 and C5, the upper extremities are correspond to C5 and T1, the thoracic wall extends from T1 to T11, the peripheral diaphragm is between T6 and T11, the abdominal wall is associated with T6–L1, lower extremities are located from L2 to S2, and the perineum from L4 to S4. By example, to address chronic pain sensations that commonly focus on the lower back and lower extremities, a specific energy field can usually be applied to a region between bony level T8 and T10. As should be understood, successful pain management and the avoidance of stimulation in unafflicted regions necessarily requires the applied electric field to be properly positioned longitudinally along the dorsal column.

Positioning of an applied electrical field relative to a physiological midline is equally important. Nerve fibers extend between the brain and a nerve root along the same side of the dorsal column as the peripheral areas the fibers represent. Pain that is concentrated on only one side of the body is "unilateral" in nature. To address unilateral pain, electrical energy is applied to neural structures on the side of a dorsal column that directly corresponds to a side of the body subject to pain. Pain that is present on both sides of a patient is "bilateral." Accordingly, bilateral pain is addressed through either an application of electrical energy along a patient's physiological midline or an application of electrical energy that transverses the physiological midline.

Pain-managing electrical energy is commonly delivered through electrodes positioned external to the dura layer surrounding the spinal cord. The electrodes are carried by two primary vehicles: a percutaneous catheter and a laminotomy lead.

Percutaneous catheters, or percutaneous leads, commonly have three or more, equally-spaced electrodes, which are placed above the dura layer through the use of a Touhy-like needle. For insertion, the Touhy-like needle is passed through the skin, between desired vertebrae, to open above the dura layer.

For unilateral pain, percutaneous leads are positioned on a side of a dorsal column corresponding to the "afflicted" side of the body, as discussed above, and for bilateral pain, a single percutaneous lead is positioned along the patient midline (or two or more leads are positioned on each side of the midline).

Laminotomy leads have a paddle configuration and typically possess a plurality of electrodes (for example, two, four, eight, or sixteen) arranged in one or more columns. An example of a sixteen-electrode laminotomy lead is shown in FIG. 1.

Implanted laminotomy leads are commonly transversely centered over the physiological midline of a patient. In such position, multiple columns of electrodes are well suited to address both unilateral and bilateral pain, where electrical energy may be administered using either column independently (on either side of the midline) or administered using both columns to create an electric field which traverses the midline. A multi-column laminotomy lead enables reliable positioning of a plurality of electrodes, and in particular, a plurality of electrode columns that do not readily deviate from an initial implantation position.

Laminotomy leads require a surgical procedure for implantation. The surgical procedure, or partial laminectomy, requires the resection and removal of certain vertebral tissue to allow both access to the dura and proper positioning of a laminotomy lead. The laminotomy lead offers a more stable platform, which is further capable of being sutured in place, that tends to migrate less in the operating environment of the human body.

Percutaneous leads require a less-invasive implantation method and, with a plurality of leads, provide a user the ability to create almost any electrode array. Although likely more stable during use, laminotomy leads do not offer an opportunity for electrode array variance due to the predetermined structure which defines their electrode arrays.

To supply suitable pain-managing electrical energy, stimulation leads are connected to multi-programmable stimulation systems, or energy sources (not shown). Typically, such systems enable each electrode of a connected stimulation lead to be set as an anode (+), a cathode (−), or in an OFF-state. As is well known, an electric current "flows" from an anode to a cathode. Consequently, using the laminotomy lead of FIG. 1 as an example, a range of very simple to very complex electric fields can be created by defining different electrodes in various combinations of (+), (−), and OFF. Of course, in any instance, a functional combination must include at least one anode and at least one cathode.

Notwithstanding the range of electric fields that are possible with conventional stimulation leads, in certain instances it is necessary to concentrate electrical energy at a particular point, or over a small region. As an example of such occasion, assume pain-managing electrical energy Is applied at or about T8 to address only localized lower back pain. At T8, however, spinal nervous tissue corresponding to the patient's lower extremities commingles with the specific spinal nervous tissue associated with the lower back. Moreover, it is common that the lower back-related spinal nervous tissue is deeply embedded within the combined spinal nervous tissue. Accordingly, it becomes desirable to focus applied electrical energy to the targeted nervous tissue to (i) reach the deeply situated target nervous tissue and (ii) avoid undesirable stimulation of unafflicted regions.

Accordingly, a need exists for a stimulation lead that includes a structural arrangement that facilitates a concentration of delivered electrical energy at a point, i.e., for a given electrode, or over a small region, i.e., for a plurality of electrodes.

SUMMARY OF THE INVENTION

At least one aspect of the present invention is drawn to a stimulation lead having a plurality of terminals, a plurality of electrodes carried by a body, and a plurality of conductors, as a conductor electrically couples one terminal with a respective electrode. The plurality of electrodes includes a first electrode and a second electrode, whereby the second electrode substantially encircles at least the first electrode.

An object of the present invention is to provide a electrical stimulation lead having at least two electrodes. Unlike known stimulation leads, however, an arrangement of the electrodes of the stimulation lead should facilitate operatively concentrating delivered electrical energy at a point, i.e., for a given electrode, or over a small region, i.e., for a plurality of electrodes.

Other objects and advantages of the present invention will be apparent to those of ordinary skill in the art having reference to the following specification together with the drawings.

BRIEF DESCRIPTION OF THE DRAWINGS

FIG. 1 is a plan view of a conventional laminotomy spinal cord stimulation lead;

FIG. 2 is a plan view of a laminotomy spinal cord stimulation lead that illustrates the fundamental principle of construction of the present invention;

FIG. 3 is a plan view of a first embodiment of a laminotomy spinal cord stimulation lead in accordance with the present invention;

FIG. 4 is a plan view of a second embodiment of a laminotomy spinal cord stimulation lead in accordance with the present invention;

FIG. 5 is a plan view of a third embodiment of a laminotomy spinal cord stimulation lead in accordance with the present invention.

DETAILED DESCRIPTION OF THE PREFERRED EMBODIMENTS

Figure 6:
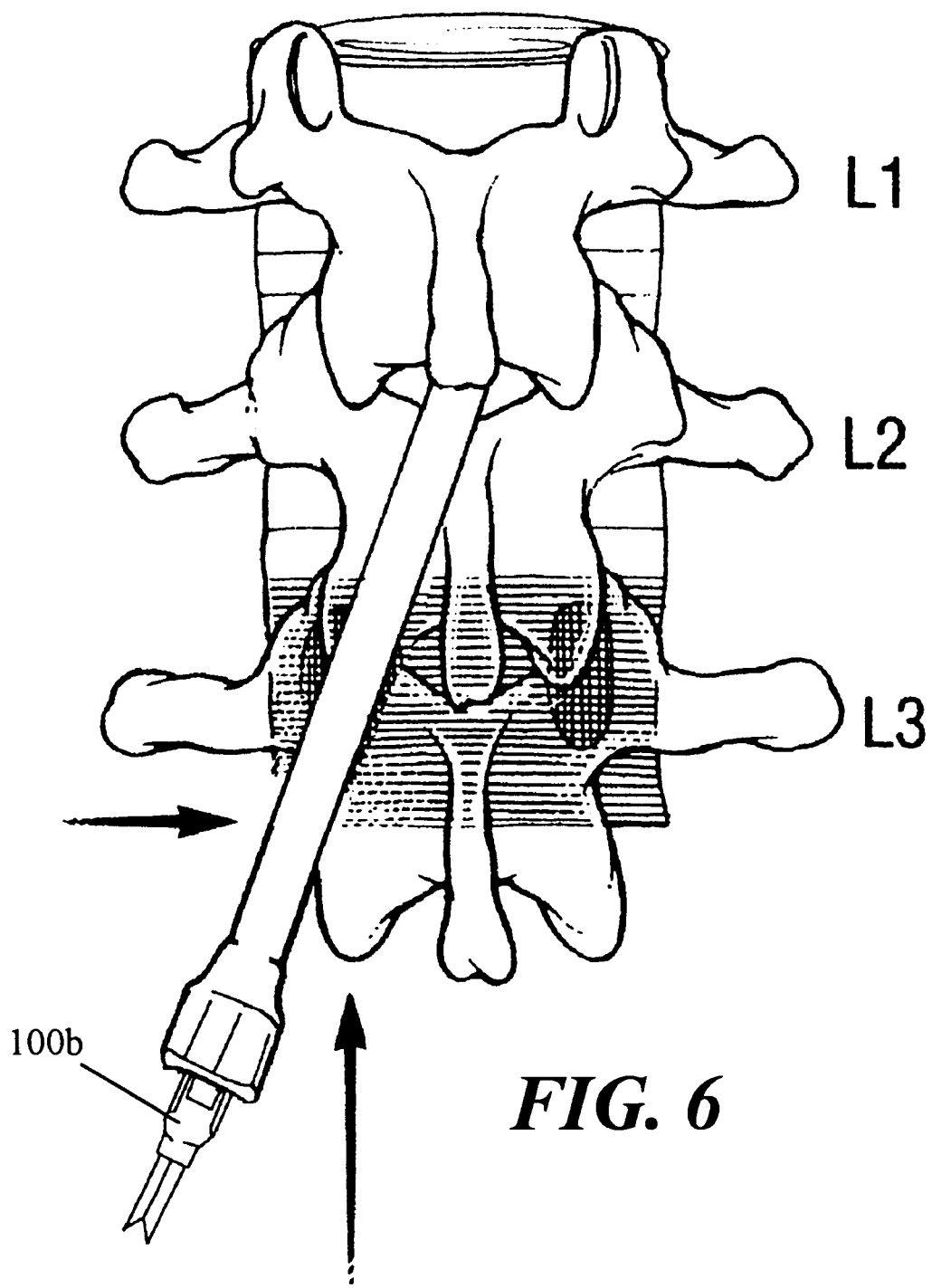
FIG. 6 illustrates a percutaneous implantation of the laminotomy spinal cord stimulation lead of FIG. 3.

Various embodiments, including preferred embodiments, will now be described in detail below with reference to the drawings.

In reference to FIG. 1, the illustrated laminotomy lead 10 includes a proximal end 12 and a distal end 14. The proximal end 12 includes a plurality of electrically conductive terminals 18, and the distal end 14 includes a plurality of electrically conductive electrodes 20 arranged within a flat, thin paddle-like structure 16. Typically, each terminal 18 is electrically connected to a single electrode 20 via a conductor 22; however, a terminal 18 can be connected to two or more electrodes 20.

Terminals 18 and electrodes 20 are preferably formed of a non-corrosive, highly conductive material. Examples of such material include stainless steel, MP35N, platinum, and platinum alloys. In a preferred embodiment, terminals 18 and electrodes 20 are formed of a platinum-iridium alloy.

The sheaths 24 and the paddle structure 16 are formed from a medical grade, substantially inert material, for example, polyurethane, silicone, or the like. Importantly, such material must be non-reactive to the environment of the human body, provide a flexible and durable (i.e., fatigue resistant) exterior structure for the components of lead 10, and insulate adjacent terminals 18 and/or electrodes 20. Additional structure (e.g., a nylon mesh, a fiberglass substrate) (not shown) can be internalized within the paddle structure 16 to increase its overall rigidity and/or to cause the paddle structure 16 to assume a prescribed cross-sectional form (e.g., a prescribed arc along a transverse direction of the paddle structure 16)(not shown).

The conductors 22 are carried in sheaths 24. In the illustrated example, each sheath 24 carries eight (8) conductors 22. Given the number of conductors 22 that are typically carried within each sheath 24, the cross-sectional area of each conductor 20 is restricted. As but one example, for a sheath 24 in accordance with the present invention, having an outer diameter of approximately 0.055 inches, each conductor 22 would be approximately 0.0065 inches in diameter.

Each conductor 22 is formed of a conductive material that exhibits desired mechanical properties of low resistance, corrosion resistance, flexibility, and strength. While conventional stranded bundles of stainless steel, MP35N, platinum, platinum-iridium alloy, drawn-brazed silver (DBS) or the like can be used, a preferred embodiment of the present invention uses conductors 22 formed of multi-strands of drawn-filled tubes (DFT). Each strand is formed of a low resistance material and is encased in a high strength material (preferably, metal). A selected number of "sub-strands" are wound and coated with an insulative material. With regard to the operating environment of the present invention, such insulative material protects the individual conductors 22 if its respective sheath 24 was breached during use. Wire formed of multi-strands of drawn-filled tubes to form conductors 22, as discussed here, is available from Temp-Flex Cable, Inc. (City, State).

In addition to providing the requisite strength, flexibility, and resistance to fatigue, conductors 22 formed of multi-strands of drawn-filled tubes, in accordance with the above description, provide a low resistance alternative to other conventional materials. Specifically, a stranded wire, or even a coiled wire, of approximately 60 cm and formed of MP35N or stainless steel or the like would have a measured resistance in excess of 30 ohms. In contrast, for the same length, a wire formed of multi-strands of drawn-filled tubes could have a resistance less than 4 ohms. Accordingly, in a preferred embodiment, each conductor 22, having a length equal to or less than 60 cm, has a resistance of less than 25 ohms. In a more preferred embodiment, each conductor 20, having a length equal to or less than 60 cm, has a resistance equal to or less than 10 ohms. In a most preferred embodiment, each conductor 20, having a length equal to or less than 60 cm, has a resistance of less than 4 ohms.

While a number of material and construction options have been discussed above, it should be noted that neither the materials selected nor a construction methodology is critical to the present invention.

The following discussion is directed to a number of examples illustrated in FIGS. 2–5. While the examples set forth a variety of variations of the present invention, it may be readily appreciated that the present invention could take any of a variety of forms and include any number of electrodes. Importantly, however, the present invention is characterized by a first electrode, or a first electrode array, that substantially encompasses or circumscribes at least one independently controlled electrode. The first electrode (or first electrode array) can operatively form an "anode guard" relative to the substantially surrounded independently controlled electrode(s). To clarify such structure, the following examples are provided.

FIG. 2 illustrates a laminotomy lead 100a featuring the fundamental principle of construction of the present invention. Specifically, the paddle structure 16 includes a plurality of electrodes 20, wherein one electrode 30 substantially surrounds another electrode 40. For this embodiment, each electrode is electrically coupled to an independent terminal (not shown), which is connectable to a programmable energy source, for example, a pulse generator (not shown). The construction and arrangement of the terminals (and related conductors, which establish the desired electrical coupling) are not in themselves unique but are consistent with that described hereinabove.

Depending upon a configuration/programmability of the energy source connected to the laminotomy lead 100a, either the electrode 30 or the electrode 40 could operatively assume a positive polarity (with the remaining electrode assuming a negative polarity) during active delivery of electrical energy therefrom. For purposes of focusing applied electrical energy, however, the electrode 30 assumes a positive polarity, whereby in such a condition the electrode 30 forms an "anode guard" relative to the encompassed electrode 40.

The electrode 30 can be constructed in a manner and from a material consistent with that used to form electrode 40. Alternatively, as longitudinal and transverse flexibility of the paddle structure 16 are desirable, it is preferred that the electrode(s) 30 be formed so as to not otherwise significantly impair the inherent flexibility of the paddle structure 16. Accordingly, the electrode 30 can be constructed using less material—in a thickness direction—than an electrode 40, formed from a conductive film/foil applied to the surface of the paddle structure 16, formed through deposition of a conductive material, constructed using a coil (FIG. 3), or formed using other like processes/techniques that are well known in the art.

An anode guard functions, in part, to laterally limit an applied electrical field, which assists in reducing extraneous stimulation of surrounding neural tissue. In this regard, neural tissue at or immediately about the cathode electrode (s) is depolarized, while neural tissue relative to the anode guard is subject to hyperpolarization. Further, an anode guard in accordance with that illustrated in FIG. 2 focuses an applied electrical field from practically every direction to any cathode-electrode(s) positioned therein. Thus, for any given drive signal from a coupled energy source, the stimulation lead of the present invention can effect a deeper application of applied energy than stimulation leads of a conventional nature.

FIG. 3 illustrates a four-channel (a "channel" represents a controllable electrical output) laminotomy stimulation lead 100b in accordance with the present invention. The stimulation lead 100b is shown having a plurality of electrodes 20, which includes an electrode 30, formed from a coil, that substantially circumscribes an electrode array formed of three electrodes 40a, 40b, and 40c.

Again, while each of the plurality of electrodes 20 could individually function as a cathode or an anode, or placed in an OFF-state, it is intended that the electrode 30, as an anode guard, assume a positive polarity. To this end, the form of an electric field generated using the electrode 30 is altered/controlled through setting each of the electrodes 40a, 40b, and 40c as a cathode, an anode, or in an OFF-state. Such control over the electrodes 40a, 40b, and 40c enables formation of a focused electrical field with a single electrode 40 as a cathode or a more diverse electrical field spread over two or more electrodes 40, whereas each electrode 40 of such plurality functions as a cathode.

Furthermore, to the extent that the benefits of an anode guard are not required, the electrode 30 may be placed in an OFF-state. In such operative configuration, the laminotomy lead 100b then functions in a manner consistent with conventional laminotomy stimulation leads.

The configuration illustrated in at least FIG. 3 enables the delivery of electrical energy to targeted nervous tissue with fewer required electrodes. Moreover, it should be noted that the narrow transverse dimension of the laminotomy lead 100b enables such laminotomy lead to be implanted percutaneously, if so desired, using a special insertion needle 200 that accommodates the greater dimensions of a laminotomy lead, for example, the laminotomy lead 100b. To this end, implantation of the present invention would be similar that described hereinabove in the context of percutaneous catheters.

FIG. 4 illustrates a laminotomy stimulation lead 100c in accordance with the present invention. The stimulation lead 100c includes a plurality of electrodes 20, which includes a first electrode array having a plurality of electrodes 30a–30d that substantially surrounds a second electrode array having a plurality of electrodes 40. The second electrode array may have a greater number of electrodes than the first electrode array as shown in FIG. 4 or an equal number of electrodes as shown in FIG. 2.

Similar to the stimulation lead 100b, the second electrode array of the stimulation lead 100c is formed of a group of individual electrodes that can respectively be set as an anode, a cathode, or in an OFF-state. Although the electrodes 40 of the stimulation lead 100c are shown in two, staggered columns, the arrangement of the electrodes 40 of the second electrode array is not critical to the present invention—the electrodes 40 of the second electrode array may assume any multiple-column arrangement.

Unlike the other embodiments illustrated, the anode guard is constructed of a first electrode array that includes electrodes 30a–30d. In a preferred embodiment, each electrode of the first electrode array extends for a length substantially equivalent to a comparable dimension of at least two of electrodes 40 of the second electrode array. Further, and generally consistent with the structures of FIGS. 2, 3, and 5, the collection of electrodes 30a–30d form an effectively continuous ring that substantially extends about the second electrode array.

Although each of the electrodes 30a–30d may be electrically independent (i.e., coupled to respective conductors/terminals), allowing each respective electrode to be an anode, a cathode, or set to an OFF-state, in consideration of practical space limitations, it may be advisable to electrically couple two or more of electrodes 30a–30d. In a simplest form, electrodes 30a–30d are electrically linked so as to maintain the same electrical state during operation and minimize the number of conductors necessary to couple the first electrode array to an energy source.

Of a final note, depending upon the form/construction of the electrodes 30a–30d, the segmented nature of the illustrated first electrode array of this embodiment would improve longitudinal flexibility of the paddle structure 16.

As additional segmentation of electrodes 30b and 30d would likewise improve transverse flexibility of the paddle structure 16, such modification is within the scope of this embodiment of the present invention.

To maintain a generally uniform electrical field between an anode guard and one or more cathode-electrodes, the distance between the one or more cathode-electrodes and the anode guard should be largely equidistant. Achieving this optimum arrangement is typically hindered by both a need that the platform structure 16 fit easily within the narrow confines of the human epidural space and a desire that the provided electrode array(s) span a significant vertebral range of spinal nervous tissue.

While a long electrode array substantially surrounded by a single anode guard electrode (or a composite anode guard) would not be operatively ineffective, an alternative to such structure is illustrated by the stimulation lead 100d of FIG. 5. Specifically, the electrodes 40 can be divided into groups 40a and 40b, and each electrode group 40a and 40b is encompassed by its own independently controlled anode guard electrode 30a and 30b.

While the invention has been described herein relative to a number of particularized embodiments, it is understood that modifications of, and alternatives to, these embodiments, such modifications and alternatives realizing the advantages and benefits of this invention, will be apparent those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. A method of providing pain managing electrical energy with an epidural stimulation lead comprising the steps of:
   implanting the epidural stimulation lead relative to a targeted nerve bundle, wherein the epidural stimulation lead further comprises:
      a first electrode array comprising a plurality of electrodes;
      a second electrode array comprising a plurality of electrodes, wherein the first electrode array encircles the second electrode array; and
      a plurality of conductors, wherein the conductors independently couple the first electrode array and the second electrode array to a programmable energy source;
   delivering pain-managing electrical energy from the programmable energy source to the first electrode array and the second electrode array through the plurality of conductors;
   laterally limiting an applied electric field associated with the delivered pain-managing electrical energy by positively biasing the first electrode array relative to the second electrode array.

2. The method of claim 1, further comprising the step of focusing the applied electric field associated with the delivered pain-managing electrical energy to the second electrode array.

3. The method of claim 1, wherein the step of laterally limiting an applied electric field associated with the delivered pain-managing electrical energy minimizes stimulating tissues which surround the targeted nerve bundle.

4. The method of claim 1, further comprising a step of depolarizing the neural tissue within the targeted nerve bundle adjacent to the second electrode array.

5. The method of claim 4, further comprising a step of hyperpolarizing the neural tissue within the targeted nerve bundle and adjacent to the first electrode array.

6. The method of claim 1, further comprising a step of implanting the lead percutaneously.

7. The method of claim 1, further comprising a step of varying, with the programmable energy source, the pain-managing electrical energy delivered to individual electrodes within the first electrode array and the second electrode array to achieve differing levels of pain reduction.

8. The method of claim 1, wherein the first electrode array and the second electrode array comprise separate arrays.

9. The method of claim 1, further comprising a step of always positively biasing the first electrode array relative to the second electrode array.

10. A method of providing pain managing electrical energy with an epidural stimulation lead comprising the steps of:
    implanting the epidural stimulation lead relative to a targeted nerve bundle, wherein the epidural stimulation lead further comprises:
       a plurality of electrode arrays that consist of:
          a first electrode array; and
          a second electrode array, wherein the first electrode array substantially encircles the second electrode array; and
       a plurality of conductors, wherein the conductors independently couple the first electrode array and the second electrode array to a programmable energy source;
    delivering pain-managing electrical energy from the programmable energy source to the first electrode array and the second electrode array through the plurality of conductors;
    laterally limiting an applied electric field associated with the delivered pain-managing electrical energy by positively biasing the first electrode array relative to the second electrode array.

11. The method of claim 10, further comprising the step of focusing the applied electric field associated with the delivered pain-managing electrical energy to the second electrode array.

12. The method of claim 10, wherein the step of laterally limiting an applied electric field associated with the delivered pain-managing electrical energy minimizes stimulating tissues which surround the targeted nerve bundle.

13. The method of claim 10, wherein the epidural stimulation lead comprises an inert body to contain the first electrode array and the second electrode array.

14. The method of claim 10, wherein neural tissue within the targeted nerve bundle and adjacent to the first electrode array becomes hyperpolarized.

15. The method of claim 10, wherein the epidural stimulation lead is implanted percutaneously.

16. The method of claim 10, wherein the programmable energy source varies the pain-managing electrical energy delivered to individual electrodes within the first electrode array and the second electrode array to achieve differing levels of pain reduction.

17. The method of claim 10, wherein the first electrode array and the second electrode array comprise separate arrays.

18. The method of claim 10, wherein the first electrode array is always positively biased relative to the second electrode array.

19. A pain-managing system comprising:
    an epidural stimulation lead implanted relative to targeted nerve bundle further comprising:

a plurality of electrode arrays that consist of:
  a first electrode array having two or more electrodes; and
  a second electrode array having two or more electrodes substantially encircled by the first electrode array;
a plurality of conductors, wherein the conductors independently couple the first electrode array and the second electrode array to a programmable energy source;
an inert body to contain the first electrode array and the second electrode array; and
an inert sheath to contain the plurality of conductors;
a programmable energy source electrically coupled to the plurality of conductors and operable to supply pain-managing electrical energy to the first electrode array and the second electrode array through the plurality of conductors;
an applied electric field associated with the delivered pain-managing electrical energy by positively biasing the first electrode array relative to the second electrode array, and wherein the applied electric field is laterally limited by the biasing.

20. The pain-managing system of claim 19, wherein the applied electric field associated with the delivered pain-managing electrical energy focuses the pain managing electrical energy to the second electrode array.

21. The pain-managing system of claim 19, wherein laterally limiting the applied electric field associated with the delivered pain-managing electrical energy minimizes stimulating tissues which surround the targeted nerve bundle.

22. The pain-managing system of claim 19, wherein the targeted nerve bundle comprises the spinal tissue.

23. The pain-managing system of claim 19, wherein the epidural stimulation lead is implanted percutaneously.

24. The pain-managing system of claim 19, wherein the programmable energy source varies the pain-managing electrical energy delivered to individual electrodes within the first electrode array and the second electrode array to achieve differing levels of pain reduction.

25. The pain-managing system of claim 19, wherein the second electrode array has a greater number of electrodes than the first electrode array.

26. A pain-managing system comprising:
  an epidural stimulation lead implanted relative to targeted nerve bundle further comprising:
    a plurality of electrode arrays that consist of:
      a first electrode array; and
      a second electrode array substantially encircled by the first electrode array, wherein the second electrode array has a greater than or equal number of electrodes as the first electrode array;
    a plurality of conductors, wherein the conductors independently couple the first electrode array and the second electrode array to a programmable energy source;
    an inert body to contain the plurality of electrodes; and
    an inert sheath to contain the plurality of conductors; and
  a programmable energy source electrically coupled to the plurality of conductors and operable to supply pain-managing electrical energy to the first electrode array and the second electrode array through the plurality of conductors.

* * * * *